United States Patent
Rahimian

(10) Patent No.: US 9,956,317 B2
(45) Date of Patent: May 1, 2018

(54) CLINICAL APPLICATIONS OF FORMULATIONS CONTAINING ADIPOSE-DERIVED STEM CELLS

(71) Applicant: Antria, Inc., Indiana, PA (US)

(72) Inventor: Shahram Rahimian, Gainesville, FL (US)

(73) Assignee: Antria, Inc., Indiana, PA (US)

( * ) Notice: Subject to any disclaimer, the term of this patent is extended or adjusted under 35 U.S.C. 154(b) by 192 days.

(21) Appl. No.: 15/131,441

(22) Filed: Apr. 18, 2016

(65) Prior Publication Data

US 2016/0228607 A1 Aug. 11, 2016

Related U.S. Application Data

(63) Continuation-in-part of application No. 14/100,360, filed on Dec. 9, 2013.

(60) Provisional application No. 62/149,144, filed on Apr. 17, 2015, provisional application No. 62/149,185, filed on Apr. 17, 2015, provisional application No. 62/149,241, filed on Apr. 17, 2015, provisional application No. 61/787,918, filed on Mar. 15, 2013, provisional application No. 61/734,514, filed on Dec. 7, 2012.

(51) Int. Cl.
| | |
|---|---|
| *C12N 9/00* | (2006.01) |
| *C12N 5/071* | (2010.01) |
| *A61L 27/38* | (2006.01) |
| *A61K 35/35* | (2015.01) |
| *A61L 27/36* | (2006.01) |
| *A61L 15/44* | (2006.01) |
| *A61L 15/40* | (2006.01) |
| *A61L 27/54* | (2006.01) |
| *C12N 5/0775* | (2010.01) |

(52) U.S. Cl.
CPC .......... *A61L 27/3687* (2013.01); *A61K 35/35* (2013.01); *A61L 15/40* (2013.01); *A61L 15/44* (2013.01); *A61L 27/3604* (2013.01); *A61L 27/3641* (2013.01); *A61L 27/3834* (2013.01); *A61L 27/3839* (2013.01); *A61L 27/54* (2013.01); *C12N 5/0667* (2013.01); *A61L 2300/412* (2013.01); *A61L 2300/64* (2013.01); *A61L 2430/34* (2013.01); *C12N 2500/14* (2013.01); *C12N 2500/16* (2013.01); *C12N 2500/22* (2013.01); *C12N 2509/00* (2013.01)

(58) Field of Classification Search
CPC ............ A61L 2430/34; A61L 27/3604; A61L 2430/24; A61L 27/3641; A61L 27/3834; A61L 2738/39; A61L 27/54; C12N 5/0667; C12N 2509/00
See application file for complete search history.

(56) References Cited

U.S. PATENT DOCUMENTS

2007/0274965 A1* 11/2007 Mitchell, II ......... C12N 5/0647
424/93.7

OTHER PUBLICATIONS

Yoshimura et al., Cell-assisted lipotransfer for cosmetic breast augmentation: Supportive use of adipose-derived stem/stromal cells. Aesthetic Plastic Surgery, vol. 32, No. 1 (Jan. 2008) pp. 48-55.*
Wu et al., An injectable adipose matrix for soft tissue reconstruction. Plastic & Reconstructive Surgery, vol. 129, No. 6 (Jun. 2012) pp. 1247-1257.*
Dulbecco's Modified Eagle's Medium/Ham's Nutrient Mixture F-12 (DME/F12) Formulation. Datasheet [online]. Sigma-Aldrich, 2017 [retrieved on Dec. 19, 2017]. Retrieved from the Internet:<URL: https://www.sigmaaldrich.com/life-science/cell-culture/learning-center/media-formulations/dme-f12. html>.*
Berry, R. and Rodeheffer, M. S., Characterization of the adipocyte cellular lineage in vivo. Nature Cell Biology, vol. 15, No. 3 (Mar. 2013) pp. 302-309.*
Church et al., Isolation and study of adipocyte precursors. Methods in Enzymology, vol. 537 (2014) pp. 31-46.*

* cited by examiner

*Primary Examiner* — Kara Johnson

(57) ABSTRACT

Methods and kits for producing cellular fractions enriched in adipose derived stem cells. Methods are provided where adipose tissue obtained from liposuction is enzymatically treated using a solution containing collagenase and divalent cations prior to the application of traditional methods of stromal-vascular fraction isolation. The enzymatic solutions may contain collagenase types I and II to a final concentration of about 0.001 mg/ml to 0.010 mg/ml. The divalent cations may be present as calcium, magnesium, and zinc chloride. The final concentration of calcium, magnesium, and zinc may range from about 0.001 to 0.1 micromolar; about 0.005 to 0.5 micromolar; and about 0.0015 to 0.15 micromolar, respectively. The enzymatic solutions may be generated using a kit where the collagenase and divalent components are held in separate containers until just prior to use. The cellular fractions isolated in this manner may be used in autologous fat grafts in therapeutic applications.

10 Claims, No Drawings

CLINICAL APPLICATIONS OF FORMULATIONS CONTAINING ADIPOSE-DERIVED STEM CELLS

CROSS-REFERENCE TO RELATED APPLICATIONS

This application claims the benefit under 35 U.S.C. § 119(e) of the earlier filing date of U.S. Provisional Patent Application Nos. 62/149,241; 62/149,144; and 62/149,185 filed on Apr. 17, 2015 and is a continuation-in-part application of U.S. patent application Ser. No. 14/100,360 (pending) filed Dec. 9, 2013, which in turn claims the benefit of the earlier filing date of U.S. Provisional Patent Application Nos. 61/734,514 filed Dec. 7, 2012; and 61/787,981 filed Mar. 15, 2013.

BACKGROUND OF THE INVENTION

1. Field of the Invention

The present invention relates generally to the fields of plastic and cosmetic surgery and regenerative medicine and specifically to the field of autologous stem-cell based therapies.

2. Description of the Background

In recent years myriad publications and discoveries have emerged describing the biology and therapeutic potential of stem cells. By definition, a stem cell is characterized by its ability to self-renew and its ability to differentiate into other cell types along multiple lineage pathways. Additionally, several studies have shown the plasticity, transdifferentiation, cyto-protectivity, angiogenicity, migration capability, cytokine production and secretion, and related immuomodulatory effects of stem cells. Accordingly, stem cells offer a large therapeutic potential in the field of regenerative medicine and tissue engineering.

Due to ethical and political controversies, safety concerns, and regulatory issues, embryonic stem cells are a disfavored source of therapeutic cells. Recent studies indicate that stem cells also exist throughout the adult body in tissues including the brain, dermis, bone marrow, periosteum, skeletal muscle, synovium, and vasculature. However, the most abundant and accessible source of adult stem cells is adipose tissue. There are over 400,000 stem cells/mL in fat tissue (>50 mil in 200 mL of fat).

Stem cells derived from adult tissues consist of Hematopoietic Stem Cells (HSCs) and Mesenchymal Stem Cells (MSCs) or Stromal Cells. Several researchers have demonstrated that mesenchymal cells within the stromal-vascular fraction of subcutaneous adipose tissue display multilineage developmental plasticity in vitro and in vivo.

With the increased incidence of obesity in the United States and abroad, subcutaneous adipose tissue is abundant and readily accessible. Approximately 400,000 liposuction surgeries are performed in the United States each year. These procedures yield anywhere from 100 mL to >3 L of lipoaspirate tissue, and this material is routinely discarded. Adipose-derived stem cells are multipotent and hold promise for a range of therapeutic applications.

These adipose-derived stem cells hold great therapeutic potential in the plastic surgery area. The autologous transplantation of fat tissue is a promising treatment for facial reconstructive surgery and soft tissue augmentation. The fat tissue provides a natural feel and look to the tissue, compared to synthetic implants. Moreover, the potential for immune system rejection of the tissue is eliminated. There are many tissue defects that cannot be treated with existing synthetic fillers and fat grafting is the only option for such indications. However, many of stem cells are being damaged or lost during the liposuction process. The idea of supplementing the fat with concentrated stem cells can replace the lost and improve graft survival.

Some problems with autologous fat transplantation remain, however. The retention and survival of transplant fat tissue is unpredictable. Generally, there is a fairly low rate of graft survival due to partial necrosis of the graft. Additionally, fat may resorb from the graft into the body. Variations in the mechanical process of fat harvesting have been undertaken to improve viability of harvested tissue, though predictability remains elusive.

Some researchers augment the transplanted fat tissue with cellular additives to promote survival. Specifically, the augmentation of fat tissue with adipose-derived stem/stromal cells has been employed to promote survival of the transplanted tissue. See Yoshimura, et al. "Cell-assisted lipotransfer for cosmetic breast augmentation: Supportive use of adipose-derived stem/stromal cells" Aesth. Plast. Surg. 32:48-55 (2008), which is hereby incorporated by reference.

The isolation of stem cells and stromal cells from adipose tissue presents a further challenge for the plastic surgeon using autologous fat grafting. The raw tissue obtained from patients may be processed to isolate a stromal vascular fraction ("SVF" as described below), which is enriched in adipose-derived stem cells. The methods for obtaining and isolating this tissue fraction should preserve the viability and promote enrichment of the stem cells. The present invention accomplishes this goal through a carefully selected enzyme-containing cocktail that may be used during cellular enrichment. By obtaining stem cell-enriched SVF, the present invention also increases the effectiveness and success of numerous medical procedures and interventions.

SUMMARY OF THE INVENTION

Generally, the present invention includes methods for isolating a portion of lipoaspirate that contains elevated numbers of several cellular components, including adipose-derived stem cells (ADSC). The present invention employs an enzymatic mixture that is augmented by the presence of specific divalent cations to isolate that fraction of lipoaspirate more effectively and efficiently.

The enzymatic mixture of the present invention may employ a blend of type I and type II collagenase and Thermolysin to extract the desired fraction from adipose tissue subsequent to liposuction. In certain embodiments, collagenases may be used at a concentration of 0.01 mg/ml. In other embodiments of the present invention the collagenase may range in concentration from about 0.001 mg/ml to about 0.010 mg/ml.

The present invention also provides that the collagenase solution contains divalent cations, which may be present as chloride salts. In certain embodiments, the divalent cations are calcium, magnesium, and zinc. The final concentration of zinc may range from about 0.0015 to about 0.15 micromolar with 0.015 micromolar being particularly useful. The concentration of magnesium may range from about 0.005 to about 0.5 micromolar with 0.05 micromolar being particularly useful. The concentration of calcium may range from about 0.001 to about 0.1 micromolar with 0.01 micromolar being particularly useful.

The above-listed components may be present as a kit. The kit may include a vial containing collagenase, which may be lyophilized. A second vial may include the divalent cations, which may be present as an aqueous solution of the chloride salts. The kit may also include a container (e.g., bag) containing physiological saline. When the contents of the two vials and bag are combined, the components reach the final concentrations in the ranges provided above.

Once that cellular fraction is isolated, it may be incorporated into untreated lipoaspirate for reinsertion into the patient as a fat graft. Such supplemented fat grafts will display greater stability and longevity compared with current state of the art care. Additionally, the isolated ADSC may be employed in numerous other therapeutic applications to achieved improved stability and outcomes for patients, such as in breast augmentation or reconstruction, wound healing, and osteoarthritis.

DETAILED DESCRIPTION OF THE INVENTION

It is to be understood that the descriptions of the present invention have been simplified to describe elements that are relevant for a clear understanding of the invention, while eliminating for purposes of clarity, other elements that may be well known.

The present invention includes formulations containing adipose-derived stem cells, methods of generating those formulations, kits for use in generating those formulations, and methods of using those formulations. The disclosure below provides particular embodiments for those inventions, though one of skill in the art will recognize multiple well-known variations of the disclosed methods, concentrations, and applications do not depart from the scope of the present invention.

Generally, the present invention includes methods for isolating a portion of lipoaspirate that contains elevated numbers of several cellular components, including adipose-derived stem cells (ADSC). While there are methods in the prior art for isolation of stem cells from adipose tissue, the present invention employs a particular enzymatic cocktail that is optimized by the presence of specific divalent cations to isolate that fraction of lipoaspirate more effectively and efficiently. Once that cellular fraction is isolated, it may be incorporated into untreated lipoaspirate for reinsertion into the patient as a fat graft. Such supplemented fat grafts will display greater stability and longevity compared with current state of the art care. Additionally, the isolated ADSC may be employed in numerous other therapeutic applications to achieved improved stability and outcomes for patients. The methods presented below are illustrative examples of an implementation of the present invention.

Upon signing the informed consent and completion of screening procedures during an initial visit to the medical professional, eligible patients may undergo a gentle (less than 1 atmosphere) liposuction procedure utilizing a standard cannula and a conventional liposuction machine to aspirate fat tissue. Approximately 50 mL-100 mL of lipoaspirate will be saved for later treatment and reformulation during the preparation phase of the protocol. Prior to liposuction, the abdominal wall is preferably infiltrated with a sterile saline solution and dilute epinephrine. The surgeon may utilize a tumescent solution that is a mixture of 1% lidocaine, and 1 mg/1000 mL epinephrine in normal saline solution. However this liposuction process can be performed without the tumescent solution in some patients. This process is a current standard of care to facilitate the aspiration process and to reduce the bleeding and pain after the procedure. This procedure can be performed under general or sedation and local anesthesia. Decisions regarding utilization of specific anesthesia techniques will be made by the medical professional undertaking the procedure.

Following aspiration, a portion of the adipose tissue from the patient may be treated to isolate a fraction enriched in adipose-derived stem cells. In certain embodiments the enrichment protocol includes three major subprocesses: preparation, incubation, and washing. Yoshimura et al. proved the efficacy of this process while extracting serovascular fraction (SVF) of adipose tissue and utilizing it to treat facial lipoatrophy (Yoshimura et al. "Cell-assisted lipotransfer for facial lipoatrophy: efficacy for clinical use of adipose-derived stem cells" *Dermatol Surg.* 34(9)1178-85 (2008), which is hereby incorporated by reference). A portion of the lipoaspirate will be collected and subject to the preparation, incubation, and washing processes. The isolation protocol will approximately take approximately sixty minutes and will preferably occur in a sterile cell processing room or other sterile environment.

Syringes (approximately 50 mL) containing the lipoaspirate may be centrifuged at 400×g for 5 minutes to separate mature adipocytes from SVF. Centrifugation will preferably yield three distinctive layers: a yellow liquid containing free fat on the top; a white-yellow fat layer in the middle; and red fluid containing erythrocytes, leukocytes, and other tissue cells at the bottom. The top and bottom layers may be removed via suction or gently pouring off the layer.

The different layers formed via centrifugation may also subsequently undergo filtration. Mesh filters having diameters of 30 μm and 100 μm may be utilized in order to selectively isolate SVF from the lipoaspirate. The 30 μm filter will enable removal of oils and small cellular debris, while the 100 μm will enable the removal of adipocytes. Hence, when used in conjunction, these filters will preferably generate a concentrated cellular component that contains ADSC. One of skill in the art will appreciate that other diameter filters (used alone or in combination) may also be used to accomplish the same goal of cellular enrichment.

Within the context of the present invention, the middle layer, which contains the SVF and adipose tissue, may then be subjected to enzymatic digestion in order to separate mature adipocytes and SVF cells. One of skill in the art will also recognize that other, non-enzymatic methods may be employed to disaggregate the lipoaspirate, including ultrasound and mechanical disruption.

The enzymatic isolation protocol of the present invention utilizes a blend of type I and type II collagenase (concentration 0.01 mg/ml) to extract the desired SVF from adipose tissue subsequent to liposuction. In certain embodiments, collagenases may be used at a concentration of 0.01 mg/ml. In other embodiments of the present invention the collagenase may range in concentration from about 0.001 mg/ml to about 0.010 mg/ml. The enzymatic mixture may also contain neutral proteases at similar concentrations. One enzymatic mixture useful within the context of the present invention is the commercially available LIBERASE.

In some embodiments of the present invention, the solution containing collagenase is supplemented with a mixture of divalent cations. In certain embodiments, the solution may contain zinc chloride, magnesium chloride, and calcium chloride. The concentration of zinc may range from about 0.0015 to about 0.15 micromolar with 0.015 micromolar being particularly useful. The concentration of magnesium may range from about 0.005 to about 0.5 micromolar with 0.05 micromolar being particularly useful. The concentration of calcium may range from about 0.001 to about 0.1 micromolar with 0.01 micromolar being particularly useful.

The present invention may also encompass a kit to be provided to medical practitioners. The kit may include multiple vials, bags, or other containers to facilitate simple practice of the methods of the present invention. In some embodiments, the present invention includes at least two vials. One vial may include about 0.01 mg to about 10 mg collagenase type I and II, with some particular embodiments include one milligram of collagenase enzyme. The collagenase may be in solution or present as a solid. When present as a solid composition, the collagenase may be present in an easily dissolvable form, such as in a lyophilized form. Another vial may include about 0.1 milliliter to about 100 milliliters of aqueous solution having high concentrations of divalent cations in the form of zinc chloride, magnesium chloride, and calcium chloride. The kit may also include a bag of saline to be employed during enzymatic isolation. The volume of saline may be appropriately selected so that the final concentration of collagenase and divalent cations falls within the ranges described above. In one embodiment, the second vial has a volume of one milliliter and the saline bag has volume of 49 milliliters such that the final concentrations of collagenase and divalent cations are at a final concentration of approximately 0.015 micromolar zinc, 0.05 micromolar magnesium, and 0.01 micromolar calcium.

The kits of the present invention may be employed in the following manner. After manual blending of syringes by the medical practitioner, collagenase-based digestion of lipoaspirate may occur at 37° C. in a shaking incubator for 30 minutes. The tissue suspension may be centrifuged for 4 minutes at 200×g and dissociated fat (supernatant) will be removed. The aforementioned centrifugation will allow the unnecessary mature adipocytes and connective tissue to separate from the SVF (Yoshimura et al. 2008). Once the SVF is extracted, a washing process may occur to maximize the purification of the cellular fraction that will be utilized in the administration of the fat graft.

Twenty mL of 0.5% dextrose solution may be added to the remaining suspension, which will then be centrifuged for 4 minutes at 200×g. The wash fluid may be removed and the same process may be repeated. Each washing step will remove some red blood cells and will reduce any residual collagenase that is present.

The SVF isolated from lipoaspirate according to the processes described above is characterized by a heterogeneous population of multiple, whole cell-types in varying concentrations. An exemplary listing of these cell-types is provided below. In certain present embodiments, the collected SVF is not genetically altered or bioengineered. Varying concentrations of the following cell types are found in SVF:
  pre-adipocytes
  endothelial progenitor cells
  smooth muscle cells
  pericytes
  fibroblasts
  adipose-derived stem cells
  T regulatory cells Once a cellular fraction of SVF containing the above-listed cells is isolated, it may be used in numerous manners and in numerous contexts. In some embodiments, the SVF may be included in a fat graft employed during cosmetic surgery. The inclusion of the SVF may increase the stability of the fat graft from the presently observed six months to up to five years. In other embodiments of the present invention, the SVF containing ADSC may be used in orthopedic applications, such as with an orthopedic insert during joint replacement. In still other embodiments, the SVF containing ADSC may be used to address wound healing and other reconstructive surgical applications. The SVF is provided from the same patient into which the fat graft, orthopedic insert, etc. is inserted, thus providing an autologous formulation/additive for treatment of a wide variety of surgical and medical conditions.

In some preliminary experiments, the present invention was employed to generate an
ADSC-enriched fraction from lipoaspirate for autologous fat grafts. Up to three months following the procedure, patients have reported no post-operative adverse effects. Further, the ADSC-augmented fat grafts have generally been stable and maintained by the patients.

Once isolated, ADSC-enriched SVF may be utilized in a numerous therapeutic applications. For example, the SVF enriched in ADSC may be included in a fat graft which may be employed during reconstructive surgical procedures. The fat graft may be used in a plastic surgery procedure designed to reconstruct a body part of a patient that was previously damaged through injury or disease. For example, the fat graft supplemented with ADSC-enriched SVF may be injected into different regions of a patient's face to improve the patient's aesthetic appearance or to repair damaged tissue. A consistent challenge confronting medical professionals is the resorption of fat grafts following injection. The inclusion of the ADSC-enriched SVF may increase the stability of the fat graft from the presently observed six months to up to five years.

As another example of therapeutic application, ADSC-enriched SVF obtained by the methods of the present invention may be used in breast augmentation procedures. Similarly, ADSC-enriched SVF may be used in breast reconstruction surgery following a lumpectomy or other surgical intervention. Depending on the patient's input and the medical practitioner's guidance, a volume of graft to be used in breast augmentation or reconstruction is determined. In some embodiments, a lipoaspirate that is approximately twice the desired graft volume will be generated from the patient. Approximately one half of the lipoaspirate may be used for the graft. The remaining portion of the lipoaspirate may be used to generate the SVF fraction as described above. The adipose tissue to be used in the graft will be kept at approximately 37 degrees Celsius until administration. Prior to administration to the patient, the fat graft may be supplemented with ADSC-enriched SVF. The ADSC-enriched SVF may be distributed substantially uniformly throughout the fat graft using common techniques. The graft may be implanted into the patient via injecting of small aliquots and the Coleman technique, which is well known in the art. Yoshimura et al. (2008; discussed above) provides an instance of how the processes, kits, and ADSC-enriched cellular fractions of the present invention may be employed in breast augmentation procedures and formulations.

As another example of therapeutic application, cellular fractions of ADSC-enriched SVF obtained by the methods of the present invention may be used in wound care. Depending on size of the wound to be treated, a volume of ADSC-enriched SVF to be used in the procedure is determined. The SVF may be generated using the procedures and compositions described above. In some embodiments, the SVF may be directly administered around the wound site, into the wound itself, and/or under the wound. In other embodiments, the SVF may be applied to or formulated into the wound dressing (e.g., bandage) prior to application of the dressing over the wound. Cherubino (2011; "Adipose-derived stem cells for wound healing applications", *Ann. Plast. Surg.*, 66: 210-15, which is hereby incorporated by reference in its entirety) and Maharlooei (2011; "Adipose tissue derived mesenchymal stem cell (AD-MSC) promotes skin wound healing in diabetic rats; *Diabetes Res. Clin. Pract.,* 93: 228-34, which is hereby incorporated by reference in its entirety) provide instances of how the processes, kits, and ADSC-enriched cellular fractions of the present invention may be employed in wound healing procedures and formulations.

As another example of therapeutic application, cellular fractions of ADSC-enriched SVF obtained by the methods of the present invention may be used in treatment of osteoarthritis. Depending on the joint or joints to be treated, a volume of ADSC-enriched SVF to be used in the procedure is determined. The SVF may be generated using the procedures and compositions described above. In some embodiments, the SVF may be directly injected into the arthritic joint. In some instances, injection of SVF may be guided by imaging techniques, such as ultrasound. ter Huurne, et al. (2012; "Anti-inflammatory and chondroprotective effects of intraarticular injection of adipose-derived stem cells in experimental osteoarthritis", *Arthritis & Rheumatism,* 64(11): 3604-13, which is hereby incorporated by reference in its entirety) and Pak (2011; "Regeneration of human bones in hip osteonecrosis and human cartilage in knee osteoarthritis with autologous adipose-tissue-derived stem cells: a case series", *J. Med. Case Reps.,* 5:296, which is hereby incorporated by reference in its entirety) provide instances of how the processes, kits, and ADSC-enriched cellular fractions of the present invention may be employed in wound healing procedures and formulations.

Similarly, cellular fractions of ADSC-enriched SVF obtained by the methods of the present invention may be used in treatment of urinary incontinence in men who have had radical prostatectomies. Depending on the severity of the condition, a volume of ADSC-enriched SVF to be used in the procedure is determined. The SVF may be generated using the procedures and compositions described above. In some embodiments, the SVF may be administered by a transurethral injection of SVF into the rhabdosphincter and submucosal space of the urethra. In some instances, injection of SVF may be guided by imaging techniques, such as ultrasound.

The preceding paragraphs provide only a small set of examples of medical applications for the ADSC-enriched SVF fraction as obtained by the present invention. Since the SVF utilized in these settings is re-administered to the patient from whom the cellular fraction is obtained, the cellular fractions of the present invention provide an invaluable tool for treatment of a wide variety of surgical and medical conditions, as will be readily appreciated by one of ordinary skill in the art.

Nothing in the above description is meant to limit the present invention to any specific concentration, order of steps, or specific duration of reaction time. Many modifications are contemplated within the scope of the present invention and will be apparent to those skilled in the art. The embodiments described herein were presented by way of example only and should not be used to limit the scope of the invention.

What is claimed is:

1. A method of performing breast augmentation, comprising the steps of:
   isolating a cellular fraction enriched in adipose-derived stem cells, comprising the steps of:
      obtaining adipose tissue from a patient by aspiration;
      combining said adipose tissue with an enzymatic solution that includes collagenase and divalent cations including calcium at a concentration from about 0.001 to about 0.1 micromolar, zinc at a concentration from about 0.0015 to about 0.15 micromolar, and magnesium at a concentration of about 0.005 to about 0.05 micromolar;
      digesting said adipose tissue for a period of time sufficient to allow digestion of said adipose tissue;
      centrifuging the digested adipose tissue to form a centrifugate; and
      isolating a stromal vascular fraction from said centrifugate;
   mixing the stromal vascular fraction with a volume of adipose tissue obtained from the patient to form a fat graft;
   injecting the fat graft into breasts of the patient.

2. The method of claim 1, wherein said collagenase comprises collagenase type I and collagenase type II.

3. The method of claim 1, wherein said collagenase is present at a concentration from about 0.001 mg/ml to about 0.010 mg/ml.

4. The method of claim 1, wherein digesting step includes placing said adipose tissue and enzymatic solution mixture in an incubator.

5. The method of claim 1, further comprising the step of washing the stromal vascular fraction following said isolating step.

6. A method of improving wound healing, comprising the steps of:
   isolating a cellular fraction enriched in adipose-derived stem cells, comprising the steps of:
      obtaining adipose tissue from a patient by aspiration;
      combining said adipose tissue with an enzymatic solution that includes collagenase and divalent cations including calcium at a concentration from about 0.001 to about 0.1 micromolar, zinc at a concentration from about 0.0015 to about 0.15 micromolar, and magnesium at a concentration of about 0.005 to about 0.05 micromolar;
      digesting said adipose tissue for a period of time sufficient to allow digestion of said adipose tissue;
      centrifuging the digested adipose tissue to form a centrifugate; and
      isolating a stromal vascular fraction from said centrifugate; and
   administering the stromal vascular fraction to a wound on the patient.

7. The method of claim 6, wherein the administering step comprises applying the stromal vascular fraction around the wound site, into the wound, or under the wound.

8. The method of claim 6, wherein the administering step further comprises:
   combining the stromal vascular fraction to a wound dressing; and
   applying the wound dressing to the wound.

9. A method of treating osteoarthritic joint of a patient, comprising the steps of:
   isolating a cellular fraction enriched in adipose-derived stem cells, comprising the steps of:
      obtaining adipose tissue from the patient by aspiration;
      combining said adipose tissue with an enzymatic solution that includes collagenase and divalent cations including calcium at a concentration from about 0.001 to about 0.1 micromolar, zinc at a concentration from about 0.0015 to about 0.15 micromolar, and magnesium at a concentration of about 0.005 to about 0.05 micromolar;

digesting said adipose tissue for a period of time sufficient to allow digestion of said adipose tissue;

centrifuging the digested adipose tissue to form a centrifugate; and isolating a stromal vascular fraction from said centrifugate; and injecting the stromal vascular fraction into the osteoarthritic joint.

10. The method of claim 9, further comprising imaging said osteoarthritic joint during said injecting step.

* * * * *